United States Patent [19]

Martel et al.

[11] 4,016,158
[45] Apr. 5, 1977

[54] CEPHALOSPORIN DERIVATIVES

[75] Inventors: Jacques Martel, Bondy; René Heymes, Romainville, both of France

[73] Assignee: Roussel-UCLAF, Paris, France

[22] Filed: Jan. 2, 1975

[21] Appl. No.: 538,189

Related U.S. Application Data

[63] Continuation-in-part of Ser. No. 320,493, Jan. 2, 1973, Pat. No. 3,962,223.

[30] Foreign Application Priority Data

| Dec. 31, 1971 | France | 71.47758 |
| Dec. 31, 1971 | France | 71.47759 |
| Dec. 31, 1971 | France | 71.47760 |
| Dec. 31, 1971 | France | 71.47761 |
| Dec. 31, 1971 | France | 71.47762 |
| Sept. 7, 1972 | France | 72.31699 |

[52] U.S. Cl. .......................... 260/243 C; 424/246
[51] Int. Cl.² ........................................ C07D 501/60
[58] Field of Search ........................... 260/243 C

[56] References Cited

UNITED STATES PATENTS

| 3,769,277 | 10/1973 | Long et al. | 260/243 C |
| 3,855,213 | 12/1974 | Dunn et al. | 260/243 C |

FOREIGN PATENTS OR APPLICATIONS 2,102,080  7/1972  France

*Primary Examiner*—Nicholas S. Rizzo
*Assistant Examiner*—James H. Turnipseed
*Attorney, Agent, or Firm*—Hammond & Littell

[57] ABSTRACT

Novel desacetoxycephalosporin derivatives of the formula

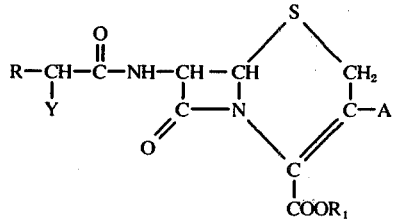

in racemic or optically active form or cis and trans forms and mixtures thereof wherein R is selected from the group consisting of aminophenyl and R', R' is selected from the group consisting of phenyl optionally substituted with at least one member of the group consisting of halogen and nitro and a 5 to 6 member heterocyclic group, Y is selected from the group consisting of amino, NHCOOR" where R" is alkyl of 1 to 5 carbon atoms, hydrogen and hydroxy, A is selected from the group consisting of

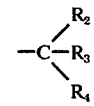

in which at least 2 of $R_2$, $R_3$ and $R_4$ are alkyl of 1 to 3 carbon atoms and the third is hydrogen or alkyl of 1 to 3 carbon atoms with the total number of carbon atoms being not greater than 5 and cycloalkyl of 3 to 7 carbon atoms optionally containing a heteroatom and $R_1$ is selected from the group consisting of hydrogen, easily acid hydrolyzable group and easily hydrogenolysis removable group, with the proviso that when R is aminophenyl Y is other than amino and NHCOOR" and $R_1$ is hydrogen and when Y is amino, $R_1$ is hydrogen and the non-toxic, pharmaceutically acceptable addition salts with organic and inorganic bases and acids where appropriate which have antibacterial activity.

7 Claims, No Drawings

CEPHALOSPORIN DERIVATIVES

PRIOR APPLICATION

This application is a continuation-in-part of our co-pending, commonly assigned application Ser. No. 320,493 filed Jan. 2, 1973 now U.S. Pat No. 3,962,223.

OBJECTS OF THE INVENTION

It is an object of the invention to provide the novel desacetoxycephalosporin compounds of formula I and the salts thereof.

It is an additional object of the invention to provide novel antibacterial compositions.

It is a further object of the invention to provide a novel method of combatting bacterial infections in warm-blooded animals.

These and other objects and advantages of the invention will become obvious from the following detailed description.

THE INVENTION

The novel products of the invention are desacetoxycephalosporin derivatives selected from the group consisting of racemates and optically active isomers of cis and trans forms and mixtures thereof of compounds of the formula

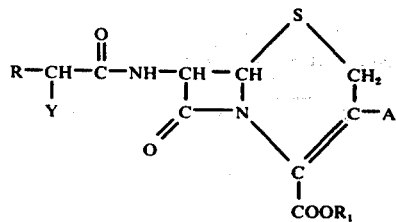

wherein R is selected from the group consisting of aminophenyl and R', R' is selected from the group consisting of phenyl optionally substituted with at least one member of the group consisting of halogen and nitro and a 5 to 6 member heterocyclic group, Y is selected from the group consisting of amino, NHCOOR" where R" is alkyl of 1 to 5 carbon atoms, hydrogen and hydroxy, A is selected from the group consisting of

in which at least 2 of $R_2$, $R_3$ and $R_4$ are alkyl of 1 to 3 carbon atoms and the third is hydrogen or alkyl of 1 to 3 carbon atoms with the total number of carbon atoms being not greater than 5 and cycloalkyl of 3 to 7 carbon atoms optionally containing a heteroatom and $R_1$ is selected from the group consisting of hydrogen, easily acid hydrolyzable group and easily hydrogenolysis removable group, with the proviso that when R is aminophenyl, Y is other than amino and NHCOOR" and $R_1$ is hydrogen and when Y is amino, $R_1$ is hydrogen and the non-toxic, pharmaceutically acceptable addition salts with organic and inorganic bases and acids where appropriate.

In the compounds of formula I, R' may be nitrophenyl, halophenyl, dihalophenyl or phenyl and a heterocyclic such as thienyl or pyridyl. $R_1$ may be hydrogen, alkyl of 1 to 6 carbon atoms such as methyl, ethyl, propyl, isopropyl, butyl, isobutyl, and tert.-butyl optionally substituted with at least one halogen such as trichloroethyl or aralkyl of 7 to 15 carbon atoms such as benzyl and p-methoxybenzyl. A may be branded alkyl of 3 to 5 carbon atoms such as isopropyl, isobutyl, or tert.-butyl or cycloalkyl of 3 to 7 carbon atoms which may contain a heteroatom such as oxygen or sulfur as cyclopentyl.

In a preferred group of compounds of formula I and their salts, R is phenyl, p-nitrophenyl, p-aminophenyl or 2-thienyl, Y is hydrogen or amino, A is isopropyl or cyclopentyl and $R_1$ is hydrogen and in another group, R is phenyl, p-nitrophenyl or 2-thienyl, Y is hydrogen or —NHCOO-tert.-butyl, A is isopropyl or cyclopentyl and $R_1$ is tert.-butyl.

Examples of suitable non-toxic, pharmaceutically acceptable bases for the addition salts are mineral bases such as sodium, or potassium hydroxide, potassium carbonate and organic bases such as cyclohexylamine, triethylamine, diphenylenediamine or dibenzyl ethylenediamine. Examples of suitable acids for the addition salts are mineral acids such as hydrogen, halides, sulfuric acid, phosphoric acid, nitric acid and boric acid and organic acids as formic acid, acetic acid, benzoic acid, salicyclic acid and p-toluene sulfonic acid.

The process for the preparation of compounds within formula I having the formula

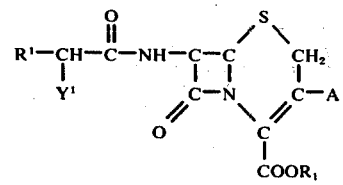

wherein $R_1$ and A have the above definition and $R^1$ is selected from the group consisting of phenyl optionally substituted with at least one halogen or nitro and a 5 to 6 heterocyclic and $Y^1$ is selected from the group consisting of NHCOOR", hydrogen and hydroxy and R" is alkyl of 1 to 5 carbon atoms comprises reacting a compound of the formula

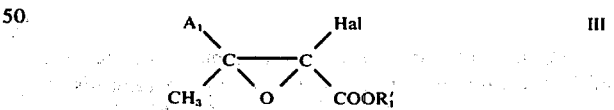

wherein $A_1$ is selected from the group consisting of methyl and A, $R'_1$ is selected from the group consisting of easily acid hydrolyzable and easily hydrogenatable removable groups and Hal is selected from the group consisting of chlorine and bromine with a dehydrohalogenating agent to form an ester of an α-methylene-α-oxo-carboxylic acid of the formula

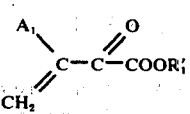

reacting the said ester in the presence of a weakly basic tertiary amine with a threo isomer, erythro isomer or mixtures thereof of a thioaminal of the formula

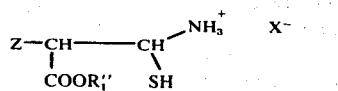 V wherein Z is selected from the group consisting of optionally substituted cyclic imido, benzoylamino and thiobenzoylamino, $R''_1$ is selected from the group consisting of alkyl of 1 to 10 carbon atoms and aralkyl of 7 to 15 carbon atoms and $X^-$ is an anion selected from the group consisting of halogen, sulfuric and sulfonic to either form a 1,3-thiazine of the formula

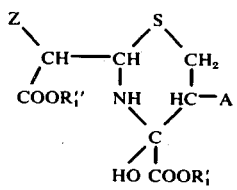 VI existing in threo or erythro form or a mixture thereof, subjecting the latter to hydrogenolysis or hydrazine treatment and then to an acid to obtain a 2,3-dihydro-1,3-thiazine of the formula

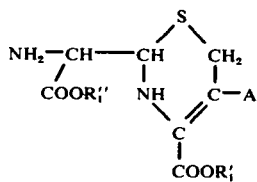 VII or to form a 1,3-thiazine of the formula

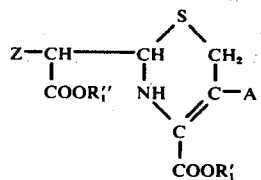 VI' existing in threo or erythro form or mixtures thereof, subjecting the latter to hydrazine or hydrogenolysis to obtain the compounds of formula VII, subjecting the latter to selective saponification with a basic agent to obtain a compound of the formula

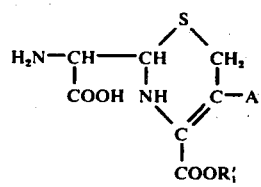 VIII in its threo or erythro form or a mixture thereof, reacting the latter with a tritylating agent to form a 2,3-dihydro1,3-thiazine of the formula

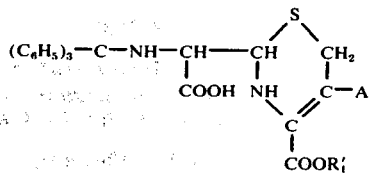 IX in its threo or erythro form or mixtures thereof, subjecting the latter to cyclization with a lactamization agent to form a compound of the formula

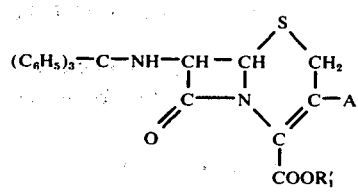 X in its cis or transform or mixtures thereof and either reacting the latter with an acid under mild conditions to form a compound of the formula

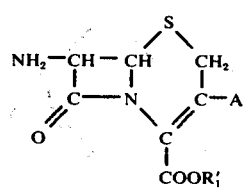 XI in its cis or transform and mixtures thereof or reacting the compound of formula X with an acid agent under severe conditions to form a compound of the formula

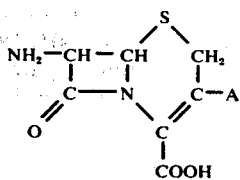 XIa in its cis or transform or mixtures thereof. The compound of formula XI can be reacted with an acid hydrolysis agent or subjected to hydrogenolysis to form the free acid of formula XIa. The compound of formula XI or XIa may be treated with a resolution agent to form the optically active isomer, if desired.

The compound of formula XI can also be reacted with a compound of the formula

 XII or a reactive derivatives thereof to form a compound of the formula

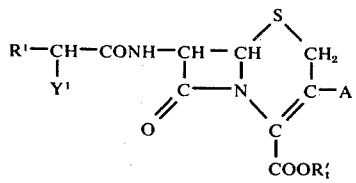

which can be subjected to acid hydrolysis or hydrogenolysis to form the corresponding free acid of the formula

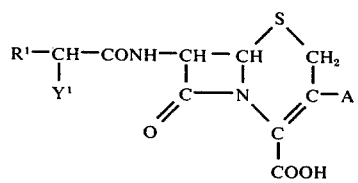

The compounds of formula XIa may also be reacted with a compound of the formula

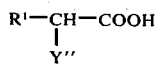

or a functional derivatives thereof wherein Y" is H or —OH to form a compound of formula IIb which may be reacted with a base to form the corresponding non-toxic, pharmaceutically acceptable addition salt.

The compounds of formula IV have an important industrial interest as they are intermediates useful in the synthesis of cephalosporin type compounds. Processes are known for obtaining compounds analogous to formula IV [Vogel, Helv., Vol. 33 (1950), p. 125] but the processes are commercially difficult in the lack of selectivity and in poor yields. The process of the invention, however, gives good yields and is selective.

The dehydrohalogenation of the compounds of formula III is preferably effected with lithium bromide or silver nitrate but other lithium and silver salts such as lithium chloride, lithium acetate, silver acetate or silver perchlorate may be used or trimethylamine salt of 0,0-dimethyl dithiophosphate or a Lewis acid such as boron trifluoride or aluminum chloride may also be used. The reaction is effected in an organic solvent, especially a good solvent for the products present such as hexamethylphosphorotriamide, dimethylsulfoxide, dimethylformamide, acetonitrile, acetone or tetrahydrofuran.

The starting products of formula III can be made by a method analogous to Darzens [C.R. Acad. Sci., Vol. 151 (1910), p. 203 and 883]. The product of formula IV may be mde by the process of British Patent No. 1,101,961.

The weakly basic tertiary amine for the condensation of the compounds of formula V and IV is pyridine or triethylamine and is effected in the presence of other tertiary amines, especially quinolein, picoline or collidine.

In the compounds of formula VI and VI' wherein Z is an optionally substituted cyclic imido group, the splitting off the Z group is preferably effected by an exchange function with hydrazine and when Z is benzoylamino or thiobenzoylamino, it is effected by hydrogenolysis in the presence of a platinum or palladium catalyst. In this case it is equally possible to effect an alkylation of the ketone or thioketone function at the first step with an alkyl sulfate or a Meerwin reactant to obtain the corresponding imino ether or imino thio ether which is then hydrolized with a mineral or organic acid such as acetic acid or dilute hydrochloric acid.

The transformation of compound VI into compound VII is terminated by acid treatment for dehydrating an intermediate product formed and not isolated of the formula

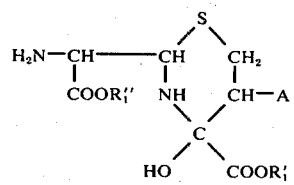

to form a compound of formula VII. Preferably, hydrochloric acid is used but other mineral acids such as sulfuric acid or hydrobromic acid as well as organic acids such as p-toluenesulfonic acid and trifluoroacetic acid may be used.

The basic agent used to saponify the $COOR_1''$ group is preferably sodium hydroxide but also useful are potassium hydroxide, lithium hydroxide, alkali metal carbonates such as sodium carbonate or potassium carbonate and the reaction is effected in the cold.

The thioaminals of formula V may be prepared by the process of French Patent No. 2,130,800 consisting of treating an enamine of the formula

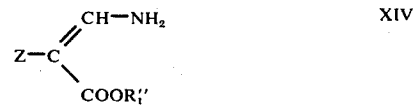

with hydrogen sulfide in the presence of a hydrohalide acid and the enamines of formula XIV may be prepared by the process of French Patent No. 1,469,529.

The tritylation agent for reaction with a compound of formula VIII is trityl chloride and the reaction is effected in the presence of an alkaline agent, preferably a tertiary amine such as trimethylamine, triethylamine, N-methylpiperidine, pyridine, N-methylpyrrolidine or quniolein.

The preferred lactamization agent is a dialkyl or dicycloalkylcarbodiimide such as dicyclohexylcarbodiimide or diisopropylcarbodiimide and the reaction is effected in a polar solvent such as nitromethane, disubstituted amide, a sulfoxide, acetone or acetonitrile and in the presence of a tertiary amine such as pyridine, coolidine or a dialkylaniline. The medium may also contain an additional solvent such as methylene chloride or chloroform.

The acid agent for the mild treatment of compounds of formula X may be a mineral or organic acid such as dilute hydrochloric acid or acetic acid and is effected in an organic solvent such as nitromethane, chloroform, methylene chloride or methanol. The reaction of a compound of formula XI to form a compound of formula XIa is preferably with a reducing agent as hydrogenolysis agent such as a zinc-acetic acid system and hydrochloric acid as the acid hydrolysis agent particularly admixed with acetic acid. In a preferred made, trifluoroacetic acid is the acid hydrolysis agent.

The acid agent for the severe treatment of compounds of formula X to form a compound of formula XIa is preferably hydrogen chloride gas, hydrofluoric acid or trifluoroacetic acid and is effected in an organic solvent such as nitromethane, chloroform, methylene chloride or methanol.

The resolution of the compounds of formula XI and XIa is effected with an optically active organic carboxylic or sulfonic acid such as tartaric acid, dibenzoyltartaric acid, composulfonic acid or glutamic acid and decomposition of the salt is effected with a mineral base such as sodium bicarbonate or an orgainc amine such as tertiary amines like triethylamine.

The acids of formula XII are preferably in the form of their functional derivatives such as the acid chloride or acid anhydride formed in situ by action of dicyclohexylcarbodiimide with the acid. Equally useful are the halides or other amides formed insitu by action with dialkylcarbodiimide or dicycloalkylcarbodiimides as well as other acid derivatives such as acid azide, acid amide or acid ester.

If the compound of formula XI is reacted with a halide of the acid of formula XII, the reaction is preferably effected in the presence of a basic agent such as alkali metal carbonates, trialkylamine or pyridine.

The reaction of a compound of formula II to one of formula IIb is effected with an acid hydrolysis agent such as hydrochloric acid alone or mixed with acetic acid and with a hydrogenolysis agent such as a reducing agent with a zincacetic acid system. Preferably, a hydrolysis agent and more preferably trifluoroacetic acid is used.

The compounds coming within the scope of formula I and having the formula

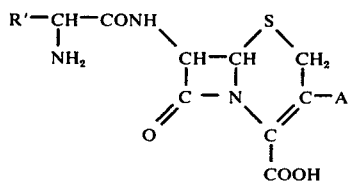

IIc or their esters or salts may be prepared by subjecting a compound of the formula

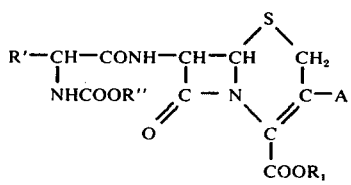

XV to an acid hydrolyzing agent or to hydrogenolysis to form the desired product of formula IIc which may be esterified or salified. The acid hydrolysis agent is preferably hydrochloric acid admixed with acetic acid and the hydrogenolysis is effected with a zinc-acetic acid system as the reducing agent. A preferred acid hydrolysis agent is trifluoroacetic acid.

Compounds with formula I having the formula

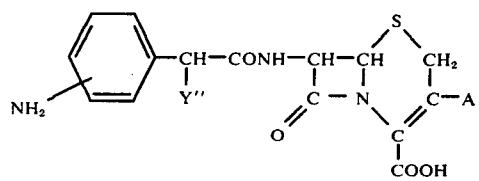

XVI or their salts or esters may be prepared by reacting a compound of the formula

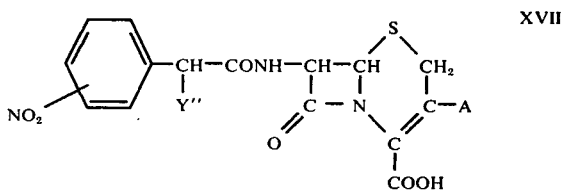

XVII with a reducing agent to form the compound of formula XVI which may be esterified or salified. The reduction is preferably effected with hydrogen in presence of a catalyst based on a platinum group metal such as palladium, preferably fixed on an inert support such as carbon, alkaline earth metal sulfate, alkaline earth carbonate, alumina, magnesia or talc. The esterification may be effected by known methods such as reaction with an alcohol in the presence of an acid agent.

Among the novel intermediate products of the invention are tert.-butyl 3-methyl-2-oxo-3-butenoate, tert.-butyl 3-isopropyl-2-oxo-3-butenoate, compounds of formula IX, and X, compounds of the formula

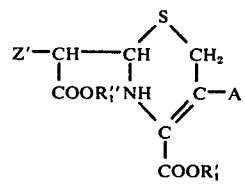

wherein Z' is amino or Z and Z, A, $R_1'$ and $R_1''$ have the above meaning and compounds of the formula

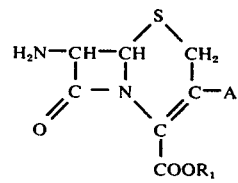

wherein $R_1$ and A have the above definitions and their salts.

The novel antibacterial compositions of the invention are comprised of an effective amount of a compound of formula I or a salt thereof and a pharmaceutical carrier. The compositions may be in the form of injectable solutions or suspensions, sterile powders for extemporaneous injectable preparations, tablets, coated tablets, capsuls, syrups, suppositaries, creams, pomades and aerosals prepared in the usual manner.

The compositions due to their antibacterial activity are useful for the treatment of staphlococci such as septicemia of staphylococcus, malignant staphylococci of the face, cutaneous staphylococcus, pyodermitis, septic sores and suppurate, anthrax, phelgm, eresypeles, primitive acute staphylococci or post grippe, bronchopneumonia and pulmonary suppurations. For example, L(+) cis 7[D(−)-α-aminophenylacetamido]-3-cyclopentyl-3-cepheme-4-carboxylic acid is active against gram positive bacteria such as staphylococci and streptococci and particularly penicillin resistant staphylococci and certain gram negative bacteria, particularly coliform bacteria.

The novel method of the invention for combatting bacterial infections in warm-blooded animals including man comprises administering an antibacterially effective amount of a compound of formula I or a non-toxic, pharmaceutically acceptable addition salt there to the warm-blooded animal. The compound may be administered orally, rectally, parenterally or locally by topical application to the skin or mucus membranes. The usual daily dose is 15 to 70 mg/kg depending upon the compound and made of administration.

In the following examples there are described several preferred embodiments to illustrate the invention. However it should be understood that the invention is not to be limited to the specific embodiments.

EXAMPLE 1

Tert.-butyl 3-isopropyl-2-oxo-3-butenoate

STEP A: terr.-butyl 2-chloro-2,3-epoxy-3-isopropyl-butanoate

A solution of 122 g of potassium tert.-butylate in 720 ml of tetrahydrofuran was added with stirring under an inert atmosphere at −20° C to a mixture of 95 g of methyl isopropyl ketone and 185 g of tert.-butyl dichloroacetate and the mixture was allowed to return to room temperature and was stirred for 2 hours. The mixture was poured into iced water and stirred after which the organic phase was removed, washed with aqueous sodium chloride solution and dried over magnesium sulfate. After passing the solution through vegetable black, the solution was concentrated to dryness to obtain 230.4 g of tert.-butyl 2-chloro-2,3-epoxy-3-isorpopyl-butanoate in the form of a colorless liquid soluble in the usual organic solvents and insoluble in water.

Analysis: $C_{11}H_{19}O_3Cl$; molecular weight = 234.725
Calculated: %C 56.29    %H 8.16    %Cl 15.10
Found:           56.2        8.3         15.6

I.R. Spectrum:
C=O at $1748^{cm-1}$ and absorption region C—O—C

STEP B: Tert.-butyl 3-isopropyl-2-oxo-3-butenoate 118 g of anhydrous lithium bromide were added under a nitrogen atmosphere at 5° C to a mixture of 117.5 g of tert.-butyl 2-chloro-2,3-epoxy-3-isopropyl-butanoate in 18.5 g of lithium carbonate and 1.15 liters of hexamethylphosphortriamide and after returning to room temperature, the mixture was stirred under a nitrogen atmosphere for 48 hours. 500 ml of distilled water were added thereto and the mixture was added to a decanting flask containing a 9:1 mixture of water and petroleum ether. After decanting, the aqueous phase was extracted with petroleum ether and the combined organic phases were washed with water, dried over magnesium sulfate, then the petroleum ether was evaporated under reduced pressure to obtain 84.6 g of tert.-butyl 3-isopropyl-2-oxo-3-butenoate in the form of a yellow liquid soluble in the usual organic solvents and insoluble in water.

U.V. Spectrum (ethanol):
Max. at 225 mμ    $E_{1cm}^{1\%} = 302$    ε = 6000

EXAMPLE 2

Threo isomer of 2-(α-carboxy-α-aminomethyl)-4-tert.-butoxycarbonyl-5-isopropyl-2,3-dihydro-1,3-thiazine STEP A: Threo and erythro isomers of 2-(α-methoxycarbonyl-α-phthalimidomethyl)-4-tert.-butoxycarbonyl-5-isopropyl-2,3-dihydro-1,3-thiazine 95 g of the thioaminal of methyl phthalimidomalonaladehydate hydrochoride (threo and erythro isomers) were added to a solution of 84.4 g of tert.-butyl-3-isopropyl-2-oxo-3-butenoate in 420 ml of ethanol cooled to −20° C and then 66 ml of an ethanol solution of 40 ml of pyridine per 100 ml of ethanolic solution were added thereto while holding a −20° C temperature. The mixture was allowed to stand at room temperature for 2 hours and then 80 ml of water were added thereto. The mixture was cooled in an ice bath for 45 minutes and was then vacuum filtered. The precipitate was washed with a 1-1 water-ethanol solution and was then empasted with petroleum ether and dried to obtain 108.1 g of threo and erythro isomers of 2-(α-methoxycarbonyl-α-phthalimidomethyl)-4-tert.-butoxycarbonyl-5-isopropyl-2,3-dihydro-1,3-thiazine which was used as is for the next step.

STEP B: Threo and erythro isomers of 2-(α-methoxycarbonyl-α-aminomethyl)-4-tert.-butoxycarbonyl-5-isopropyl-2,3-dihydro-1,3-thiazine 55 ml of a solution of 2M hydrazine hydrate in dimethylformamide were added with stirring under a nitrogen atmosphere to a solution of 46.1 g of the product from Step A in 46 ml of chloroform cooled to 0° C and the mixture was stirred for 1 hour at room temperature. 600 ml of ether and 30 ml of acetic acid were added thereto and the mixture, after standing for 1 hour, was filtered. The filter was washed with ether and the filtrate was added to 400 ml of aqueous saturated sodium bicarbonate solutions. The mixture was stirred for 10 minutes and was then decanted. The organic phase was washed with water and the wash waters were extracted with ether. The combined organic phases were dried over magnesium sulfate and the solvent was evaporated off under reduced pressure to obtain threo and erythro isomeric mixture of 2-(α-methoxycarbonyl-α-aminomethyl)-4-tert.-butoxycarbonyl-5-isopropyl -2,3-dihydro-1,3-thiazine.

STEP C: Threo isomer of 2-(α-carboxy-α-aminomethyl)-4-tert.-butoxycarbonyl-5-isopropyl-2,3-dihydro-1,3-thiazine The product of Step B was dissolved under a nitrogen atmosphere with stirring in 100 ml of acetone and the 100 ml of N sodium hydroxide was added to the solution cooled at 0° C. The mixture stood for 20 minutes and then 6.3 ml of acetic acid were added thereto and the mixture was stirred for 1 hour. The mixture was vacuum filtered and the precipitate was empasted with ether, vacuum filtered and dried under reduced pressure. The dried residue was ground, empasted with acetone, then ether and dried under reduced pressure to obtain 13.2 g of the threo isomer of 2-(α-carboxy-α-aminomethyl)-4-tert.-butoxycarbonyl-5-isopropyl-2,3-dihydro-1,3-thiazine melting at 150° C with decomposition. The product occurred in the form of yellowish white crystals slightly soluble in water and ethanol and insoluble in ether.

Analysis: $C_{14}H_{24}O_4N_2S$;  molecular weight = 316.42
Calculated:   %C 53.15  %H 7.65   %N 8.86   %S 10.12
Found:        52.9      7.6       9.2       9.9

U.V. Spectrum (ethanol):
Max. at 280–281 nm          $E_{1cm}^{1\%} = 90$    $\epsilon = 2900$ I.R. Spectrum (Nujol):
Absorption area OH/NH, C=O at $1729^{cm-1}$ and absorption towards $1698-1679^{cm-1}$.

EXAMPLE 3

Tert.-butyl DL cis 7-tritylamino-3-isopropyl-3-cepheme-4-carboxylate

STEP A: Threo isomer of 2-(α-carboxy-α-tritylaminomethyl)-4-tert.-butoxycarbonyl-5-isopropyl-2,3-dihydro-1,3-thiazine A solution of 10.7 g of tritychloride in 70 ml of chloroform was added with stirring under a nitrogen atmosphere to a solution of 11.1 g of the threo isomer of 2-(α-carboxy-α-aminomethyl)-4-tert.-butoxycarbonyl-5-isopropyl-2,3-dihydro-1,3-thiazine in 140 ml of chloroform and 10.8 ml of triethylamine cooled to −50° C and after standing at −50° C for 30 minutes, the temperature was raised to room temperature. The mixture was evaporated to dryness and the residue was dissolved in 170 ml of methanol. 21.5 ml of 2N hydrochloric acid were added thereto and after stirring at 0° C for 15 minutes, the mixture was vacuum filtered. The precipitate was washed with methanol and then with ether and was dried to obtain 9.1 g of the threo isomer of 2-(α-carboxy-α-tritylaminomethyl)-4-tert.-butoxycarbonyl-5-isopropyl-2,3-dihydro-1,3-thiazine melting at 180° C with decomposition. The product occurred in the form of colorless crystals soluble in chloroform, slightly soluble in ethanol and insoluble in water.

Analysis: $C_{33}H_{38}O_4N_2S$;  molecular weight = 558.75
Calculated:   %C 70.94  %H 6.86   %N 5.01   %S 5.73
Found:        71.0      6.7       4.8       5.9

I.R. Spectrum (Nujol):
Presence of C=O, free and associated NH and aromatic bands U.V. Spectrum (ethanol + dioxane):
Inflex. towards 227 nm      $E_{1cm}^{1\%} = 269$
Max. at 264 nm              $E_{1cm}^{1\%} = 55$
Max. at 273 nm              $E_{1cm}^{1\%} = 55$
Max. at 287 nm              $E_{1cm}^{1\%} = 56$    $\epsilon = 3,130$ STEP B: Tert.-butyl DL cis 7-tritylamino-3-isopropyl-3-cepheme-4-carboxylate A solution of 6.4 g of dicyclohexylcarbodiimide in 52 ml of chloroform was added to a mixture of 14.9 g of the product of Step A in 15 ml of chloroform and 1500 ml of nitromethane cooled to 0° C and after returning the temperature to room temperature, 27 ml of pyridine were added to the mixture which was stirred for 15 hours under a nitrogen atmosphere. The insolubles were removed by vacuum filtration and after rinsing the filter with ether, the combined filtrates were evaporated to dryness. The residue was dissolved in 60 ml of methylene chloride and the solution was vacuum filtered again. The filtrate was evaporated to dryness and the residue was suspended in 95 ml of ethanol. The mixture was stirred at room temperature for 15 minutes and then for 15 minutes after cooling. The mixture was vacuum filtered and the recovered precipitate was washed with ethanol, then with petroleum ether and dried to obtain 8.3 g tert.-butyl DL cis 7-tritylamino-3-isopropyl-3-cepheme-4-carboxylate.

For analysis, 13.6 gm of the product were added to 41 ml of methylene chloride and the solution was filtered. 200 ml of ethanol were added to the filtrate and the mixture was concentrated to a small volume and was vacuum filtered. The precipitate was washed with ethanol and then with petroleum ether and dried to obtain 12.5 g of pure product melting at 227° C. The product occurred in the form of colorless crystals soluble in chloroform, slightly soluble in ethanol and insoluble in water.

Analysis: $C_{33}H_{36}O_3N_2S$;  molecular weight = 540.74
Calculated:   %C 73.31  %H 6.71   %N 5.18   %S 5.92
Found:        73.1      6.7       5.1       5.7

I.R. Spectrum (chloroform):
Presence of β-lactam at $1773^{cm-1}$, conjugated ester at $1721^{cm-1}$ aromatics and C=C at 1653, 1616 and $1597^{cm-1}$.

U.V. Spectrum (ethanol):
Inflex. towards 228 nm      $E_{1cm}^{1\%} = 297$
Max. at 263 nm              $E_{1cm}^{1\%} = 121$    $\epsilon = 6550$

EXAMPLE 4

Tert.-butyl cis 7-amino-3-isopropyl-3-cepheme-4-carboxylate

STEP A: Tert.-butyl DL cis 7-amino-3-isopropyl-3-cepheme-4-carboxylate

A solution of 7.57 g of tert.-butyl DL cis 7-tritylamino-3-isopropyl-3-cepheme-4-carboxylate in 14 ml of chloroform, 8.4 ml of methanol and 2.8 ml of ethanolic solution of 10N hydrochloric acid stood for 20 minutes and after the addition of 84 ml of ether, the mixture was vacuum filtered. The crystals recovered were washed with ether and dried to obtain 4.6 g of the hydrochloride of tert.-butyl DL cis-7-amino-3-isopropyl-3-cepheme-4-carboxylate. 3 g of the said hydrochloride were added with stirring to 20 ml of methylene chloride and 25 ml of aqueous 10% sodium bicarbonate solution and after decanting the organic phase, the aqueous phase was extracted with methylene chloride. The organic phases were dried over magnesium sulfate and vacuum filtered. The filter was washed with methylene chloride and the filtrate was evaporated to dryness to obtain 2.54 g of tert.-butyl DL cis-7-amino-3-isopropyl-3-cepheme-4-carboxylate melting at 114° C. The product occurred in the form of colorless crystals soluble in alcohols, chloroform and ether and insoluble in water.

Analysis: $C_{14}H_{22}O_3N_2S$;  molecular weight = 298.41
Calculated:   %C 56.36  %H 7.43   %N 9.39   %S 10.73
Found:        56.1      7.3       9.3       10.4

I.R. Spectrum (chloroform):
Presence of $NH_2$ 3404 and $3333^{cm-1}$, of β-lactam at $1773^{cm-1}$ and conjugated ester at $1721^{cm-1}$.

U.V. Spectrum:

| Ethanol: Max. at 269 nm | $E_{1cm}^{1\%} = 236$ | $\epsilon = 7050$ |
| Ethanol-N/10 HCl: max. at 258 nm | $E_{1cm}^{1\%} = 212$ | $\epsilon = 6300$ |

STEP B: Resolution of Ester

A mixture of 2.38 g of tert.-butyl DL cis 7-amino-3-isopropyl-3-cepheme-4-carboxylate and 1.3 of D (—) tartaric acid in 8 ml of methanol was heated to reflux and after cooling to 25° C, the mixture was vacuum filtered. The precipitate was washed with a 1-1 methanol-ether mixture and then with ether and dried to obtain 1.394 of the tartrate of tert.-butyl L (+) cis 7-amino-3-isopropyl-3-cepheme-4-carboxylate.

The latter product was stirred with 15 ml of aqueous 10% sodium bicarbonate solution and 15 ml of methylene chloride and the organic phase was decanted. The aqueous phase was extracted with methylene chloride and the combined organic phases were dried over magnesium sulfate and evaporated to dryness to obtain 0.919 g of L (+) enantiomorph of tert.-butly cis 7-amino-3-isopropyl-3-cepheme-4-carboxylate in the form of colorless crystals soluble in chloroform and insoluble in water. The product melted at 132° C and had a specific rotation $[\alpha]_D^{20} = +47.5° \pm 2.5°$ (c = 0.6% in chloroform). Concentration of the mother liquors and decomposition of the residual tartrate gave 0.87 g of D(—) enantiomorph of the said ester melting at 120° C and having a specific rotation $[\alpha]_D^{20} = -35° \pm 2°$ (c = 1% in chloroform).

EXAMPLE 5

DL cis 7-amino-3-isopropyl-3-cepheme-4-carboxylic acid

A current of gaseous hydrogen chloride was passed for 15 minutes through a mixture of 541 mg of tert.-butyl DL cis 7-tritylamino-3-isporopyl-3-cepheme-4-carboxylate in 11 ml of nitromethane on an ice bath and the mixture was then evaporated to dryness. The residue was taken in ether and was vacuum filtered. The precipitate was washed with ether, dried and dissolved in 1 ml of water. The pH was adjusted to 4 with pyridine addition and the mixture was vacuum filtered. The crystals recovered were washed with water, then acetone and ether and dried to obtain 204 mg of DL cis 7-amino-3-isopropyl -3-cepheme-4-carboxylic acid mleting at 230° C with decomposition. The product occurred as colorless crystals slightly soluble in water, ethanol and acetone and insoluble in ether.

Analysis: $C_{10}H_{14}O_3N_2S$;  molecular weight = 242.30
| Calculated: | %C 49.58 | %H 5.83 | %N 11.57 | %S 13.20 |
| Found: | 49.3 | 5.9 | 11.5 | 13.4 |

I.R. Spectrum (Nujol):
Presence of β-lactam at $1779^{cm-1}$, absorption region $COO^{(-)}$, C=C at 1642, 1623, 1543 and $1519^{cm-1}$.

U.V. Spectrum:
| Ethanol Inflex towards 245 nm | $E_{1cm}^{1\%} = 221$ | |
| Max. at 267 nm | $E_{1cm}^{1\%} = 253$ | |
| Ethanol-N/10 HCl: Max. at 249 nm | $E_{1cm}^{1\%} = 222$ | $\epsilon = 5400$ |

EXAMPLE 6

DL cis 7-p-nitrophenylacetamido-3-isopropyl-3-cepheme-4-carboxylic acid

STEP A: Tert.-butyl DL cis 7-p-nitrophenylacetamido-3-isopropyl-3-cepheme-4-carboxylate A mixture of 3.78 g of p-nitrophenylacetic acid, 2.34 g of dichlohexylcarbodiimide, 26 ml of nitromethane and 10.4 ml of chloroform was stirred under nitrogen for 20 minutes at room temperature and was vacuum filtered to remove insolubles. The filter was washed with a 1-1 nitromethane-chloroform mixture and then 1.74 g of the hydrochloride of tert.-butyl DL cis 7-amino-3-isopropyl-3-cepheme-4-carboxylate and 2.1 ml of pyridine were added to the combined filtrates. After stirring for 1 hour under a nitrogen atmosphere, the mixture was vacuum filtered and the precipitate was washed with nitromethane, empasted with ether and dried to obtain 2.3 g of tert.-butyl DL cis 7-p-nitrophenylacetamido-3-isopropyl-3-cepheme-4-carboxylate melting at 250° C.

STEP B: DL cis 7-p-nitrophenylacetamido-3-isopropyl-3-cepheme -4-carboxylic acid A solution of 1.06 g of the ester of Step A in 10 ml of trifluoroacetic acid stood for 5 minutes and was then evaporated to dryness. The residue was taken up in benzene and evaporated to dryness. The residue was empasted with 20 ml of ether, stirred for 15 minutes, vacuum filtered, washed with ether and dried to obtain 790 mg of DL cis 7-p-nitrophenylacetamido-3-isopropyl-3-cepheme-4-carboxylic acid melting at 190° C decomposition. The product occurred as colorless crystals slightly soluble in ethanol and insoluble in water.

Analysis: $C_{18}H_{19}O_6N_3S$;  molecular weight = 405.43
| Calculated: | %C 53.33 | %H 4.72 | %N 10.37 | %S 7.90 |
| Found: | 53.1 | 4.9 | 10.3 | 7.6 |

I.R. Spectrum (Nujol):
Presence of β-lactam at $1772^{cm-1}$, of carbonyls at $1703^{cm-1}$ (acid) and $1656^{cm-1}$ (amide), of NH/OH at 3464 and $3276^{cm-1}$ and C=C bands.

U.V. Spectrum (ethanol):
| Max. at 268 nm | $E_{1cm}^{1\%} = 405$ | $\epsilon = 16,400$ |

EXAMPLE 7

DL cis 7-p-aminophenylacetamido-3-isopropyl-3-cepheme-4-carboxylic acid

A mixture of 400 mg of activated carbon, 2.8 ml of a solution of 2% palladium chloride in water and 12 ml of water was purged with nitrogen and then a hydrogen current was passed therethrough until saturated. The mixture was vacuum filtered and the resulting palladized activated carbon was rinsed with water.

The catalyst was added to a solution of 406 mg of DL cis 7-p-nitrophenylacetamido-3-isopropyl-3-cepheme-4-carboxylic acid in 3.8 ml of dimethylformamide and 1.12 ml of N hydrochloric acid and a current of hydrogen was passed therethrough until saturated. The mixture was filtered and the filter was washed with a 50—50 water-ethanol solution containing a few drops of hydrochloric acid. The filtrate was evaporated to dryness and the residue was taken up in 3 ml of water.

Ammonium formate was added thereto to a pH of 4.5 and the mixture was stirred 5 minutes and vacuum filtered. The precipitate was empasted with water and dried to obtain DL cis 7-p-aminophenylacetamido-3-isopropyl-3-cepheme-4-carboxylic acid melting at 150° C with decomposition. The product occurred as ocre crystals slightly soluble in water, ethanol and chloroform and insoluble in ether.

Analysis: $C_{18}H_{21}O_4N_3S$;  molecular weight = 375.45
Calculated:   %C 57.59   %H 5.64   %N 11.20   %S 8.53
Found:            57.3       5.8       11.3       8.3

I.R. Spectrum (Nujol):
Presence of $\beta$-lactam at $1773^{cm-1}$, of amide at $1647^{cm-1}$, of secondary amide at $1533^{cm-1}$, of $COO^{(-)}$ at $1589^{cm-1}$ and absorptions in the OH/NH region.

U.V. Spectrum:
Ethanol: Max. at 244 nm    $E_{1cm}^{1\%}=385$    $\epsilon = 14,400$
Inflex. towards 269 nm     $E_{1cm}^{1\%}=188$
Ethanol-N/10HCl: Max. at 256 nm    $E_{1cm}^{1\%}=161$    $\epsilon = 6,000$

EXAMPLE 8

DL cis 7-(2'-thienyl)-acetamido-3-isopropyl-3-cepheme-4-carboxylic acid

STEP A: Tert.-butyl DL cis 7-(2'-thienyl)-acetamido-3-isopropyl-3-cepheme-4-carboxylate A solution of 386 mg 2-thienylacetic acid chloride in 2 ml of chloroform was added under nitrogen to a stirred cooled mixture of 670 mg of the hydrochloride of tert.-butyl DL cis 7-amino-3-isopropyl-3-cepheme-4-carboxylate, 6.7 ml of chloroform and 0.61 ml of pyridine and after standing for 10 minutes in the cold, the mixture stood at room temperature for 45 minutes. The mixture was washed with N hydrochloric acid (pH 1) and the organic phase was decanted and washed with water. The aqueous phase was extracted with methylene chloride and the combined organic phases were added to 4 ml of 10% sodium bicarbonate dissolved in water. The mixture was stirred and the organic phase was decanted and washed with water. The aqueous phase was extracted with methylene chloride and the combined organic phasese were dried over magnesium sulfate and evaporated to dryness. The residue was taken up in 15 ml of ether, stirred and vacuum filtered. The product was rinsed with ether and dried to obtain 624 mg of tert.-butyl DL cis 7-(2'-thienyl)-acetamido-3-isopropyl-3-cepheme-4-carboxylate melting at 170° C. Concentration of the mother liquor and crystallization of the residue from isopropyl ether gave a second crop of 120 mg of the product melting at 170° C.

STEP B: DL cis 7-(2'-thienyl)-acetamido-3-isopropyl-3-cepheme-4-carboxylic acid

A solution of 744 mg of the ester of Step A in 7.4 ml of trifluoroacetic acid stood for 5 minutes and was evaporated to dryness. The residue was taken up in benzene and was evaporated to dryness. The product was empasted with ether, vacuum filtered, washed with ether and dried to obtain 490 mg of DL cis 7-(2'-thienyl)-acetamido-3-isopropyl-3-cepheme-4-carboxylic acid melting above 200° C. The product occurred as colorless crystals soluble in methanol, slightly soluble in ethanol and insoluble in water.

Analysis: $C_{16}H_{18}O_4N_2S$;   molecular weight = 366.46
Calculated:    %C 52.46   %H 4.95   %N 7.65   %S 17.47
Found:             52.5       5.0       7.5       17.2

I.R. Spectrum (Nujol):
Presence of $\beta$-lactam at $1776^{cm-1}$, of conjugated acid C=O at $1709^{cm-1}$, of amide at 1658 and $1645^{cm-1}$, of conjugated C=C at 1631 and $1550^{cm-1}$ and of secondary amide.

U.V. Spectrum:
Ethanol: Max at 237–238 nm    $E_{1cm}^{1\%}=367$
Inflex. towards 263 nm        $E_{1cm}^{1\%}=184$
Ethanol-N/10HCl: Max. at 237–238 nm   $E_{1cm}^{1\%}=368$
Inflex. towards 263 nm        $E_{1cm}^{1\%}=174$

EXAMPLE 9

L (+) cis 7-[D (−)-α-aminophenylacetamido]-3-isopropyl-3-cepheme-4-carboxylic acid STEP A: Tert.-butyl L(+) cis 7-[D(−)-α-tert.-butoxycarbamidophenylacetamido]-3-isopropyl-3-cepheme-4-carboxylate 0.895 g of tert.-butyl L (+) cis 7-amino-3-isopropyl-3-cepheme-4-carboxylate and 1 ml of pyridine were added to a solution of 3.01 g of D (−)-α-tert.-butoxycarbamidophenylacetic acid in 20 ml of chloroform and 1.32 of dicyclohexylcarbodiimide which had been cooled and stirred for 10 minutes and the mixture was then stirred for 4 hours. The insolubles were removed by filtration and the filtrate was washed with ether. The filtrate was evaporated to dryness and the residue was taken up in 20 ml of ether and filtered again. 30 ml of ether were added to the filtrate and the ether phase was washed with N hydrochloric acid, with water, with a 10% sodium bicarbonate in water solution and finally water. The filtrate was dried over magnesium sulfate and evaporated to dryness to obtain tert.-butyl L (+) cis 7-]D(−)-α-tert.butoxycarbamidophenylacetamido]-3-isopropyl-3-cepheme-4-carboxylate.

STEP B:  L(+) cis 7-[D(−)-α -aminophenylacetamido]-3-isopropyl-3-cepheme-4-carboxylic acid A solution of the ester of Step A in 20 ml of trifluoroacetic acid stood for 15 minutes at room temperature and was evaporated to dryness under reduced pressure. The residue was taken up in benzene and evaporated to dryness and the residue was dissolved in 10 ml of water. Pyridine was added to adjust the pH to 6 and crystallization took place at room temperature for 15 minutes and then was cooled for 30 minutes. The mixture was vacuum filtered and the precipitate was washed with water, ethanol and then ether and dried. The product was dissolved in 6 ml of ethanol and 0.4 ml of triethylamine and the solution was vacuum filtered. The filter was washed with ethanol and 0.4 ml of acetic acid was added to the filtrate which was then filtered. The product was washed with ethanol, then with ether and dried to obtain 0.745 g of L(+) cis 7-[D(−)-α-aminophenylacetamido]-3-isopropyl-3-cepheme-4-carboxylic acid melting at 200° C with decomposition and had a specific rotation $[\alpha]_D^{20} = +90° \pm 3°$ (c = 0.5% in 0.1N hydrochloric acid). The product occurred as colorless crystals slightly soluble in ethanol and insoluble in ether.

Analysis: $C_{18}H_{21}O_4N_3S,O,5\ C_2H_5\ OH$: molecular weight = 398.40
Calculated:   %C 57.27   %H 6.07   %N 10.55   %S 8.05
Found:        57.1       6.2       10.5       7.9

I.R. Spectrum (Nujol):
Presence of conjugated COOH at $1693^{cm-1}$, of β-lactam and secondary amids.

U.V. Spectrum (ethanol):
Max. at 258 nm   $E_{1cm}^{1\%} = 157$   $\epsilon = 5900$

EXAMPLE 10

L(+) 6R, 7R 7-[R(−)-α-aminophenylacetamido]-3-cyclopentyl-3-cepheme-4-carboxylic acid STEP A: Tert.-butyl 3-cyclopentyl-2-oxo-3-butenoate A mixture of 12.3 g of cyclopentylmethyl ketone and 18.5 g of tert.-butyl dichloroacetate was cooled to −30° C with stirring under an inert atmosphere and a solution of 12.2 g of potassium tert.-butylate in 60 ml of tetrahydrofuran was added thereto at the said temperature. After returning to room temperature, hexane and water were added and the organic phase was separated, washed with water and dried over magnesium sulfate. The solvents were evaporated off to leave an oily residue of tert.-butyl 2-chloro-3-cyclopentyl-2,3-epoxybutanoate. 26.5 g of the latter product was added to a solution of 3 g of lithium carbonate and 20 g of lithium bromide in 100 ml of hexamethylphosphorotriamide and after stirring for 1 hour at room temperature, petroleum ether and water were added thereto. The organic phase was washed with water, dried over magnesium sulfate and filtered. The solvent was evaporated to obtain an oily residue which was tert.-butyl 3-cyclopentyl-2-oxo-3-butenoate which was used as is for the next step.

STEP B: Threo isomer of 2-(α-methoxycarbonyl-α-phthalimidomethyl)-4-tert.-butoxycarbonyl-5-cyclopentyl-4-hydroxy-1,3-thiazine 14 g of hydrochloride of the thioaminal of methyl phthalimidomalonalaldehyde were added to a solution cooled at 0° C of 20 g of the product of Step A in 50 ml of ethanol and 6.3 ml of triethylamine were added dropwise thereto while keeping a 0° C temperature. The mixture was stirred at this temperature for 1 hour and was vacuum filtered. The recovered precipitate was washed with 50—50 ethanol-water solution, then with isopropyl ether and dried at 40° C under reduced pressure to obtain 11 g of the threo isomer of 2-(α-methoxycarbonyl-α-phthalimidomethyl)-4-tert.-butoxycarbonyl-5-cyclopentyl-4-hydroxy-1,3-thiazine melting at 140° C. The product occurred as colorless crystals soluble in methylene chloride and chloroform, slightly soluble in alcohol and ether and insoluble in water.

Analysis: $C_{25}H_{32}N_2O_7S$;   molecular weight = 504.6
Calculated:     59.51   %H 6.39   %N 5.55   %S 6.35
Found:          59.3    6.4       5.3       6.6

I.R. Spectrum (chloroform):
Presence of hydroxy at $3529^{cm-1}$, of phthalimido at 1782 and $1726^{cm-1}$, of conjugated ester at $1726^{cm-1}$ and ester in nitrogen at $1756^{cm-1}$.

STEP C: Threo isomer of 2-(α-methoxycarbonyl-α-aminomethyl)-4-tert.-butoxycarbonyl-5-cyclopentyl-2,3-dihydro-1,3,-thiazine .HCl 86 g of the product of Step B were added to 95 ml of a solution of 2M hydrazine hydrate in dimethylformamide and after stirring for 1 hour at room temperature, 800 ml of ether containing 17 ml of acetic acid were added thereto. The mixture was stirred for 2 hours and vacuum filtered and the recovered precipitate was washed with ether. The combind organic phases were washed with aqueous solution saturated with sodium bicarbonate, then with water, dried over magnesium sulfate and slightly treated with an ethanolic solution of 10N hydrochloric acid. The precipitate formed was recovered by vacuum filtration and was then washed with ether and dissolved in 60 ml of warm methanol. 100 ml of ethyl ether and 200 ml of isopropyl ether were added thereto to precipitate and recover 29.6 g of threo isomer of 2-(α-methoxycarbonyl-α-aminomethyl)-4-tert.-butoxycarbonyl-5-cyclopentyl-2,3-dihydro-1,3-thiazine hydrochloride melting at 150° C. The product occurred as colorless crystals soluble in methanol and ethanol, slightly soluble in ethyl acetate and insoluble in ether.

Analysis: $C_{17}H_{29}ClN_2O_4S$;   molecular weight = 392.94
Calculated:   %C 51.95   %H 7.44   %N 7.14   %Cl 9.02   %S 8.16
Found:        51.7       7.6       7.4       8.8        8.2

STEP D: 2-(α-carboxy-α-aminomethyl)-4-tert.-butoxycarbonyl-5-cyclopentyl-2,3-dihydro-1,3-thiazine 38 ml of 2N sodium hydroxide were added with stirring under a nitrogen atmosphere to a solution cooled to 0° C of 15.7 g of the hydrochloride of Step C in 80 ml of acetone and 16 ml of water and after stirring at 5° C for 10 minutes, carbon dioxide was bubbled therethrough for 20 minutes. The precipitate formed was recovered by vacuum filtration and was washed with water, with acetone and then with ether and dried at 40° C under reduced pressure to obtain 12 g of 2-(α-carboxy-α-aminomethyl)-4-tert.-butoxycarbonyl-5-cyclopentyl-2,3-dihydro)-1,3-thiazine melting at 170° C. The product occurred as colorless crystals soluble in water, slightly soluble in ethanol and insoluble in ether.

Analysis: $C_{16}H_{26}N_2O_4S$;   molecular weight = 342.46
Calculated:      %C 56.12   %H 7.65   %N 8.8   %S 9.36
Found:           55.9       7.9       8.0      9.7

STEP E: Threo isomer of 2-(α-carboxy-α-tritylaminomethyl)-4-tert.-butoxycarbonyl-5-cyclopentyl-2,3-dihydro-1,3-thiazine 0.85 ml of triethylamine were added to a solution cooled to −55° C of 1.7 g of the product of Step D in 22 ml of chloroform and then a solution of 1.7 g of trityl chloride in 10 ml of chloroform was added dropwise. Another 0.85 ml of triethylamine was added and then the rest of trityl chloride solution. After standing at room temperature, the mixture was evaporated under reduced pressure and the residue was taken up in ether and water. The organic phase was decanted and was washed with dilute hydrochloride acid and water. The organic phase was dried over magnesium sulfate and evaporated under reduced pressure. The residue was triturated with isopropyl ether and crystallized. The residue was added to hexane and the crystals were recovered by vacuum filtration and were dried to obtain 1.5 g of the threo isomer of 2-($\alpha$-carboxy-$\alpha$-tritylaminomethyl)-4-tert.-butoxycarbonyl-5-cyclopentyl-2,3-dihydro-1,3-thiazine melting at 190° C. The product occurred as colorless crystals soluble in chloroform, slightly soluble in methanol and ethanol and insoluble in water.

Analysis: $C_{35}H_{40}N_2O_4S$; molecular weight = 584.7

| | %C | %H | %N | %S |
|---|---|---|---|---|
| Calculated: | 71.89 | 6.90 | 4.79 | 5.48 |
| Found: | 72.2 | 6.8 | 4.5 | 5.4 |

STEP F: Tert.-butyl DL cis 7-tritylamino-3-cyclopentyl-3-cepheme-4-carboxylate 7.2 g of dicyclohexylcarbodiimide were added to a solution cooled to 5° C of 19.5 g of the product of Step E in 140 ml of chloroform and 600 ml of nitromethane and after stirring for 15 minutes, 12 ml of pyridine were added. The mixture was stirred overnight at room temperature and the insolubles were removed by vacuum filtration and were rinsed with ether. The filtrate was evaporated and the residue was taken up in 50 ml of methylene chloride and vacuum filtered. The filtrate was evaporated to dryness and the residue was taken up in ether and crystallization effected. The precipitate was recovered by vacuum filtration to obtain 13.1 g of tert.-butyl DL cis 7-trithylamino-3-cepheme-4-carboxylate melting at 210° C. The product occurred as colorless crystals soluble in methylene chloride and chloroform, slightly soluble in methanol, ethanol and ether and insoluble in water.

Analysis: $C_{35}H_{38}N_2O_3S$; molecular weight = 566.7

| | %C | %H | %N | %S |
|---|---|---|---|---|
| Calculated: | 74.18 | 6.76 | 4.94 | 5.65 |
| Found: | 74.0 | 7.1 | 4.7 | 5.5 |

STEP G: Tert.-butyl DL cis 7-amino-3-cyclopentyl-3-cepheme-4-carboxylate 2 ml of an ethanolic solution of 10N hydrochloric acid were added to a solution of 5.8 g of the product of Step F in 10 ml of chloroform and 6 ml of methanol and after standing 10 minutes at room temperature, the mixture was diluted with 60 ml of ether. The precipitate was vacuum filtered and washed with ether and added to an aqueous sodium bicarbonate solution. The mixture was extracted with methylene chloride and the organic phase was dried and concentrated to dryness. The residue was added to isopropyl ether and the crystals obtained by vacuum filtration were washed with hexane to obtain 3.1 g of tert.-butyl DL cis 7-amino-3-cyclopentyl-3-cepheme-4-carboxylate melting at 150° C. The product occurred as colorless crystals soluble in isopropyl ether and insoluble in water and hexane.

Analysis: $C_{16}H_{24}N_2O_3S$; molecular weight = 324.45

| | %C | %H | %N | %S |
|---|---|---|---|---|
| Calculated: | 59.24 | 7.46 | 8.64 | 9.86 |
| Found: | 59.4 | 7.7 | 8.5 | 9.6 |

STEP H: DL cis 7-amino-3-cyclopentyl-3-cepheme-4-carboxylic acid

A current of gaseous hydrogen chloride was passed through a mixture of 585 mg of the product of Step G and 12 ml of nitromethane cooled to 0° C for 15 minutes and the mixture was evaporated to dryness under reduced pressure. The residue was taken up in ether and the crystals were recovered by vacuum filtration. The residue was dissolved in 2 ml of ethanol and 1 ml of water and pyridine was added to a pH of 4. The mixture was agitated until crystallization appeared and the crystals were recovered by vacuum filtration, were rinsed with ethanol and dried to obtain 249 mg of DL cis 7-amino-3-cyclopentyl-3-cepheme-4-carboxylic acid melting at 250° C. The product occurred as colorless crystals slightly soluble in ethanol and insoluble in water and ether.

Analysis: $C_{12}H_{16}N_2O_3S$; molecular weight = 268.34

| | %C | %H | %N | %S |
|---|---|---|---|---|
| Calculated: | 53.72 | 6.01 | 10.44 | 11.93 |
| Found: | 53.5 | 5.9 | 10.7 | 11.9 |

STEP I: L(+) 6R, 7R 7-[R(—)-$\alpha$-aminophenylacetamido]-3-cyclopentyl-3-cepheme-4-carboxylic acid 1.3 g of dicyclohexylcarbodiimide were added with stirring to a solution cooled to 5° C of 3 g of R (—)-$\alpha$-tert.-butoxycarbamidophenyl acetic acid in 20 ml of chloroform and after stirring the mixture for 10 minutes, 0.5 ml of pyridine and 1.6 g of the product of Step G were added thereto. The mixture was stirred for 1 hour at room temperature and was vacuum filtered. The filtrate was evaporated to dryness and the residue was taken up in a 4-1 ethyl acetate-methylene chloride mixture. The organic solution was washed with water and aqueous sodium bicarbonate solution, dried over magnesium sulfate and evaporated to dryness. The residue was triturated with isopropyl ether to obtain 2.7 g of colorless crystals of tert.-butyl 7-[R (—)-$\alpha$-tert.-butoxycarbamidophenyl acetamido]-3-cyclopentyl-3-cepheme-4-carboxylate diastereoismers.

The said crystals were suspended in 25 ml of ether and the crystals were vacuum filtered and dried to obtain 1.3 go of product melting at 185° C. The ether filtrate was evaporated to dryness and the residue was disintegrated in hexane to obtain 1.2 g of product melting at 125° C and 1 g of this product was dissolved in 10 ml of trifluoroacetic acid. The solution stood for 1 hour at room temperature and was then evaporated to dryness under reduced pressure. The residue was added to 20 ml of isopropyl ether and the crystals formed were recovered by vacuum filtration and stirred with water containing pyridine. The crystals were vacuum filtered and crystallized from 50-50 ethanol-water solution to obtain 495 mg of L(+) 6R, 7R 7-[R(—)-$\alpha$-aminophenylacetamido]-3-cyclopentyl-3-cepheme-4-carboxylic acid melting at 200° C with decomposition and having a specific rotation $[\alpha]_D^{20} = +82° \pm 3°$ (c = 0.5% in 0.1N hydrochloric acid). The product occurred as colorless crystals slightly soluble in water and ethanol and insoluble in ether.

Analysis: $C_{20}H_{23}N_3O_4S$; molecular weight = 401.5
Calculated: %C 59.84 %H 5.78 %N 10.46 %S 7.99
Found: 59.9 5.7 10.8 7.9

EXAMPLE 11

DL cis 7-p-nitrophenylacetamido-3-cyclopentyl-3-cepheme-4-carboxylic acid

STEP A: Tert.-butyl DL cis 7-p-nitrophenylacetamido-3-cyclopentyl-3-cepheme-4-carboxylate A mixture of 1.45 g of p-nitrophenylacetic acid and 880 mg of dicyclohexylcarbodiimide, 10 ml of nitromethane and 4ml of chloroform was stirred under nitrogen and after standing at room temperature for 45 minutes, the insolubles were removed by vacuum filtration and rinsed with chloroform. 650 mg of the product of Step G of Example 10 were added to the combined filtrates and after the addition of 0.8 ml of pyridine, the mixture was stirred under a nitrogen atmosphere for 1 ½ hours. The organic solution was treated with aqueous N hydrochloric acid, then with aqueous sodium bicarbonate solution and then water, dried over magnesium sulfate and evaporated to dryness. The residue was taken up in ether and the crystals formed were vacuum filtered and rinsed with ether and dried to obtain 905 mg of tert.-butyl DL cis 7-p-nitrophenylacetamido-3-cyclopentyl-3-cepheme-4-carboxylate in the form of colorless crystals.

STEP B: DL cis 7-p-nitrophenylacetamido-3-cyclopentyl-3-cepheme-4-carboxylic acid A solution of 244 mg of the ester of Step A in 2.5 ml of trifluoroacetic acid stood at room temperature for 8 minutes and was then evaporated to dryness under reduced pressure. The residue was taken up in benzene and was evaporated to dryness. The residue was triturated with ether and crystallization was effected. The crystals were vacuum filtered, washed with ether and dried to obtain 174 mg of DL cis 7-p-nitrophenylacetamido-3-cyclopentyl-3-cepheme-4-carboxylic acid melting at 170° C. The product occurred as colorless crystals slightly soluble in ethanol and insoluble in ether and water.

Analysis: $C_{20}H_{21}N_3O_6S$; molecular weight = 431.47
Calculated: %C 55.68 %H 4.91 %N 9.74 %S 7.42
Found: 55.5 5.2 9.6 7.3

EXAMPLE 12

DL cis 7-p-aminophenylacetamido-3-cyclopentyl-3-cepheme-4-carboxylic acid

A mixture of 900 mg of activated carbon, 2.8 ml of 2% palladium chloride aqueous solution and 27 ml of water was stirred and a current of hydrogen was bubbled therethrough until 43 ml of hydrogen were absorbed. The mixture was vacuum filtered and the palladized activated carbon was rinsed with water. The said carbon was added to a solution of 900 mg of DL cis 7-p-nitrophenylacetamido-3-cyclopentyl-3-cepheme-4-carboxylic acid in 7 ml of dimethylformamide and 2.5 ml of N hydrochloric acid and after purging with nitrogen, a current of hydrogen was passed therethrough with stirring. The catalyst was filtered off and the filtrate was evaporated to dryness. The residue was added to water and ammonium formate was added thereto and the crystals were vacuum filtered and dried at 50° C to obtain DL cis 7-p-aminophenylacetamido-3-cyclopentyl-3-cepheme-4-carboxylic acid as colorless crystals soluble in ethanol, slightly soluble in water and insoluble in ether.

EXAMPLE 13

DL cis 7-(2'-thienyl)-acetamido-3-cyclopentyl-3-cepheme-4-carboxylic acid

STEP A: Tert.-butyl DL cis 7-(2'-thienyl)-acetamido-3-cyclopentyl-3-cepheme-4-carboxylate Using the procedure of Step A of Example 11, 1.14 g of 2-thienylacetic acid were reacted to obtain 810 mg of tert.-butyl DL cis 7-(2'-thienyl)-acetamido-3-cyclopentyl-3-cepheme-4-carboxylate in the form of colorless crystals.

STEP B:

Using the procedure of Step B of Example 11, 225 mg of tert.-butyl DL cis 7-(2'-thienyl)-acetamido-3-cyclopentyl-3-cepheme-4-carboxylate were reacted to obtain 130 mg of DL cis 7-(2'-thienyl)-acetamido-3-cyclopentyl-3-cepheme -4-carboxylic acid melting at 220° C. The product occurred as colorless crystals slightly soluble in water and insoluble in ether.

Analysis: $C_{18}H_{20}N_2O_4S$; molecular weight = 392.50
Calculated: %C 55.10 %H 5.14 %N 7.14 %S 16.31
Found: 55.0 5.2 7.1 16.1

PHARMACOLOGICAL STUDY

The antibiotic activity was determined by the diffusion method in a gelose medium at a pH of 7. The following Table expresses the minimum concentration of inhibition in mcg/ml (CMI) for the products against different microbial strains.

TABLE I

| Products | Staph. aureus oxford U.C. 1061 P(+) | Staph. U.C. 1128 P(−) | Strept. hemoly. Todd Hewitt | Strept. Fecalis 5432 | Bac. Subt. | Escher. Coli UC 1020 | Escher. Coli UC 1261 | Pseudo-monas |
|---|---|---|---|---|---|---|---|---|
| DL cis 7-(2'-thienyl)acetamido-3-isopropyl-3-cepheme-4-carboxylic acid | 2 | 5 | 10 | >40 | 0.4 | >200 | >200 | >200 |
| DL cis 7-p-nitro- | | | | | | | | |

TABLE I-continued

| Products | Staph. aureus oxford U.C. 1061 P(+) | Staph. U.C. 1128 P(−) | Strept. hemoly. Todd Hewitt | Strept. Fecalis 5432 | Bac. Subt. | Escher. Coli UC 1020 | Escher. Coli UC 1261 | Pseudo-monas |
|---|---|---|---|---|---|---|---|---|
| phenylacetamido-3-isopropyl-3-cepheme-4-carboxylic acid | 0.4 | 2 | 5 | >40 | 0.2 | >200 | >200 | >200 |
| DL cis 7-p-amino-phenylacetamido-3-isopropyl-3-cepheme-4-carboxylic acid | 2 | 10 | 10 | >40 | 0.05 | >200 | >200 | >200 |
| L(+) cis 7-(D(−) α-aminophenyl-acetamido)-3-isopropyl-3-cepheme-4-carboxylic acid | 0.4 | 2 | 10 | 20 | 0.2 | 100 | 40–100 | >100 |
| DL cis 7-p-nitro-phenylacetamido-3-cyclopentyl-3-cepheme-4-carboxylic acid | 0.2 | 0.4 | >40 | >40 | 0.1 | | | |
| L(+) 6R, 7R 7-[R(−) α-aminophenyl-acetamido]-3-cyclopentyl-3-cepheme-4-carboxylic acid | 0.4 | 1 | 10 | 20 | 0.05 | | | |
| DL cis 7-(2′-thienyl)acetamido-3-cyclopentyl-3-cepheme-4-carboxylic acid | 1 | 1 | >40 | 20 | 1 | | | |
| Cephalexin | 2 | 10 | 10 | 60 | 0.2 | 20 | 20 | |

P(+) - penicillin sensitive
P(−) - penicillin resistant

Table I shows that the compounds of the invention possess a good activity against pathogenic microorganisms, particularly against staphylococcus.

Using the same procedure as in Table I, the minimum inhibition concentration in mcg/ml was determined against different microbial strains with L(−) cis 7-[D(−)-α-aminophenylacetamido]-3-isopropyl-3-cepheme-4-carboxylic acid (product A) of Example 9. The results are reported in Table II.

TABLE II

| Organism | Product A 24h | Product A 48h | Product A 72h | Cephalexine 24h | Cephalexine 48h |
|---|---|---|---|---|---|
| *Diplococcus pneumoniae* 735 | 0.4 | 1 | 1 | | |
| *Staphylococcus aureus* | | | | | |
| A8P | 1 | 3 | 10 | 2 | 5 |
| 54146 | 1 | 1 | 2 | | |
| 9482 | 1 | 2 | 2 | 1 | 1 |
| 4546 | 0.6 | 2 | 3 | 1 | 3 |
| 9729 | 2 | 2 | 5 | 2 | 3 |
| 1098 | 0.4 | 1 | 3 | | |
| 8514 | 1 | 2 | 2 | | |
| 017 | 2 | 5 | 15 | | |
| 980 | >40 | | | | |
| *Frottis nasal* | 2 | 3 | 10 | | |
| 9373 | 1 | 3 | 5 | 2 | 3 |
| 397 | 2 | 5 | 10 | | |
| 5880 | 2 | 3 | 10 | | |
| 889 | 5 | 10 | 20 | 5 | 10 |
| 9561 | 1 | 3 | 10 | | |
| *Streptococcus hemolyticus* | | | | | |
| 905 | 2 | 2 | 2 | | |
| 561 | 0.6 | >40 | | | |
| 920 | 2 | 2 | 3 | | |
| *Escherichia coli* | | | | | |
| Taylor | 40 | 40 | 60 | | |
| 9927 | 100 | >100 | | | |
| 5369 | 30 | 40 | 100 | | |
| 51 | 100 | >100 | | | |
| 5003 | 40 | 40 | 40 | | |
| 5524 | 60 | 60 | 60 | | |
| 9957 | 40 | 100 | 100 | | |
| 070 | 40 | 40 | 40 | | |
| 1751 | 30 | 30 | 30 | | |
| 3019 | 30 | 40 | 40 | | |
| 8497 | 100 | 100 | 100 | | |
| 1718 | 40 | 40 | 60 | | |
| 4965 | 30 | 40 | 40 | | |
| 152 | 30 | 30 | 40 | | |
| *Proteus mirabilis* | | | | | |
| 8029 | 60 | >100 | | | |
| 1668 | 100 | >100 | | | |

TABLE II-continued

| Organism | Product A | | | Cephalexine | |
|---|---|---|---|---|---|
| | 24h | 48h | 72h | 24h | 48h |
| 6194 | 60 | 80 | >100 | | |
| 8065 | 60 | >100 | | | |
| 3113 | 100 | >100 | | | |
| Klebsiella pneumoniae | | | | | |
| 52145 | 30 | 60 | >100 | | |
| Salmonella typhimurium | | | | | |
| 420 | 60 | 60 | >100 | | |
| brandebourg 550 | 30 | 30 | 40 | | |
| Shigella flexneri | 20 | 40 | 40 | | |
| Shigella sonnei | 30 | 30 | 30 | | |

The bactericidal activity of product A was ascertained by determining the number of germs still alive after treatment with increasing doses of antibiotic on a liquid media. From the cultures in tubes having 72 hours (previously described method), were placed on agar in Petri dishes a constant sample of the last tube having grown and of the following tubes where no more growth in transillumination is observed. After 48 hours of culture in the Petri dishes, the number of colonies was ascertained. The results are reported in Table II.

+++ indicates that all the germs are still alive. + indicates that it remains some colonies. − indicates that it does not remain any germ.

TABLE II

| Strain | Inhibitory Concentration in μg/ml | | | | | | | | | | |
|---|---|---|---|---|---|---|---|---|---|---|---|
| | 1 | 2 | 3 | 5 | 10 | 15 | 20 | 30 | 40 | 60 | 100 |
| Staphylococcus aureus 54146 | +++ | + | 3 colonies | − | | | | | | | |
| Staphylococcus aureus 9482 | +++ | 1 colonie | 2 colonies | − | | | | | | | |
| Staphylococcus aureus 1098 | +++ | +++ | 1 colonies | − | | | | | | | |
| Staphylococcus aureus 8514 | +++ | +++ | a few colonies | − | | | | | | | |
| Streptococcus hemolyticus 905 | +++ | − | − | | | | | | | | |
| Streptococcus hemolyticus 920 | | +++ | − | | | | | | | | |
| Diplococcus pneumoniae 735 | +++ | − | − | | | | | | | | |
| Shigella sonnei | | | | | | | +++ | + | 9 colonies | − | |
| Escherichia coli 070 | | | | | | | | +++ | − | | |
| Escherichia coli 4965 | | | | | | | | +++ | − | | |

The in vivo antibacterial activity for product A was determined in mice with an experimental staphylococcia. 50 male mice weighing 20 to 23 g were divided into 5 groups of 10 mice each and all were infected interperitoneally with 0.5 ml of a 15 hour culture of Staphylococcus aureus in Pasteur nutritive broth diluted 1/3 with distilled water. Each mouse received product A orally 1 hour and 5 hours after the infection. The number of animals surviving was then determined and the results of Table III show that product A has a good antibacterial activity in this test when administered orally.

TABLE III

| Dose on mg (repeated two times) | Mortality at: | | | | Mice living on 8th day | |
|---|---|---|---|---|---|---|
| | 6h30 | 8h | 10h | 22h | 70h | |
| 0 | 1 | 1 | 6 | 2 | | 0/10 |
| 0.5 | | | 1 | 1 | 1 | 7/10 (70%) |
| 1.0 | | | | | 1 | 9/10 (90%) |
| 2.0 | | | | | | 10/10 (100%) |
| 3.0 | | | | | | 10/10 (100%) |

The oral toxicity of product A was determined on homogenous groups of 10 male rats weighing 100 to 110 g by administering orally a 0.25% by weight dispersion of product A in an aqueous suspension of carboxymethyl cellulose with an esophagus probe. The animals had been without food for 6 hours, (drink at libitum) and the dose was a constant volume of 10 ml/kg of the suspension to give 800 mg/kg of product A. Under these test conditions, the $LD_{50}$ was greater than 800 mg/kg. During the observation period, none of the rats presented any abnormal symptoms. The rats in the test were held in a place in which the air was filtered and sterilized by ultraviolet light and the temperature was held at 22° ± 1° C with a controlled humidity.

The transcutaneous toxicity of product A was determined with a 0.25% by weight dispersion of product A in an aqueous suspension of carboxymethyl cellulose at varying concentrations and the suspension was administered transcutaneously to homogenous lots of 10 male rats weighing 100 to 110 g (drink at libitum) at a constant volume of 10 ml/kg of body weight at doses of 800 and 1600 mg/kg. The rats were held under the same conditions as in the previous test and none of the rats showed any abnormal symptoms. On the 8th day, all the rats were still alive which means the $LD_{50}$ dose in this test is above 1600 mg/kg.

Various modification of the compositions and method of the invention may be made without departing from the spirit or scope thereof and it should be understood that the invention is to be limited only as defined in the appended claims.

We claim:

1. A compound selected from the group consisting of desacetoxycephalosporins of the formula

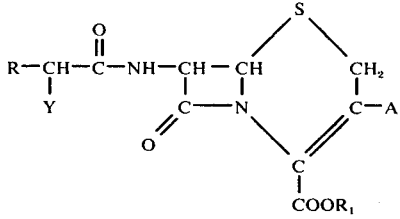

in racemic or optically active form or cis and trans forms and mixtures thereof wherein R is selected from the group consisting of aminophenyl and R', R' is selected from the group consisting of phenyl optionally substituted with one member of the group consisting of halogen and nitro and a 5 to 6 member heterocyclic group selected from the group consisting of thienyl and pyridyl, Y is selected from the group consisting of amino, NHCOOR'', where R'' is alkyl of 1 to 5 carbon atoms, hydrogen and hydroxy, A is selected from the group consisting of in which at least 2

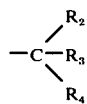

of $R_2$, $R_3$ and $R_4$ are alkyl of 1 to 3 carbon atoms and the third is hydrogen or alkyl of 1 to 3 carbon atoms with the total number of carbon atoms being not greater than 5 and cycloalkyl of 3 to 7 carbon atoms and $R_1$ is selected from the group consisting of hydrogen, alkyl of 1 to 6 carbon atoms, trichloroethyl, benzyl and methoxybenzyl with the proviso that when R is aminophenyl Y is other than amino and NHCOOR'' and $R_1$ is hydrogen and when Y is amino, $R_1$ is hydrogen and the non-toxic, pharmaceutically acceptable addition salts with organic and inorganic bases and acids where appropriate.

2. A compound of claim 1 wherein A is selected from the group consisting of isopropyl and tertiary butyl, $R_1$ is hydrogen, R is selected from the group consisting of phenyl, p-nitrophenyl, p-aminophenyl and 2-thienyl and Y is selected from the group consisting of hydrogen and amino.

3. A compound of claim 1 wherein A is selected from the group consisting of isopropyl and tertiary butyl, $R_1$ is tert.-butyl, R is selected from the group consisting of phenyl, p-nitrophenyl and 2-thienyl and Y is selected from the group consisting of hydrogen and NHCOO tert.-butyl.

4. A compound of claim 1 which is selected from the group consisting of L(+) cis 7-[D(−)-α-aminophenylacetamido]-3-isopropyl-3-cepheme-4-carboxylic acid and its non-toxic, pharmaceutically acceptable salts.

5. A compound of claim 1 wherein A is cycloalkyl of 3 to 7 carbon atoms with the further proviso that when Y is amino, $R_1$ is hydrogen.

6. A compound of claim 5 wherein R is selected from the group consisting of phenyl, p-nitrophenyl, p-aminophenyl and 2-thienyl, Y is selected from the group consisting of hydrogen and amino, A is cyclopentyl and $R_1$ is hydrogen.

7. A compound of claim 5 which is selected from the group consisting of L(+), 6R, 7R 7-[R(−)-α-aminophenylacetamido]-3-cyclopentyl-3-cepheme-4-carboxylic acid and its non-toxic, pharmaceutically acceptable salts.

* * * * *